United States Patent [19]
Matyas

[11] Patent Number: 5,885,254
[45] Date of Patent: Mar. 23, 1999

[54] REPLACEABLE FLEXIBLE PROTECTIVE COVER FOR AN INFUSION DEVICE

[76] Inventor: Melanie E. Matyas, 301 N. Duane Ave., San Gabriel, Calif. 91775

[21] Appl. No.: 850,165

[22] Filed: May 2, 1997

Related U.S. Application Data

[63] Continuation-in-part of Ser. No. 368,097, Jan. 3, 1995, Pat. No. 5,776,106.
[51] Int. Cl.$^6$ .............................. A61M 5/00; A61M 25/00
[52] U.S. Cl. ............................................ 604/180; 604/174
[58] Field of Search ..................................... 604/180, 174, 604/51, 177

[56] References Cited

U.S. PATENT DOCUMENTS

| | | | |
|---|---|---|---|
| 4,519,793 | 5/1985 | Galindo | 604/180 |
| 4,633,863 | 1/1987 | Filips | 604/180 |
| 4,898,587 | 2/1990 | Mera et al. | 604/180 |
| 5,074,847 | 12/1991 | Greenwell et al. | 604/180 |
| 5,112,313 | 5/1992 | Sallee | 604/180 |
| 5,336,204 | 8/1994 | Matyas . | |
| 5,685,859 | 11/1997 | Kornerup | 604/180 |

Primary Examiner—Michael Buiz
Assistant Examiner—William W. Lewis
Attorney, Agent, or Firm—Christie, Parker & Hale, LLP

[57] ABSTRACT

A replaceable flexible protective cover for an infusion device formed from a transparent membrane adhesive on one side affixable to the skin of a person to surround at least a part of the infusion device, and the membrane includes a portion through which a portion of the device passes and grips the infusion device to assure stability as well as added waterproof characteristic to the cover.

44 Claims, 5 Drawing Sheets

REPLACEABLE FLEXIBLE PROTECTIVE COVER FOR AN INFUSION DEVICE

RELATION TO COPENDING PATENT APPLICATION

This patent application is a continuation-in-part to U.S. patent application Ser. No. 08/368,097, filed on Jan. 3, 1995, U.S. Pat. No. 5,776,106.

FIELD OF THE INVENTION

This invention relates to a replaceable and flexible protective cover to create a waterproof seal around an infusion device to isolate it from the outside air and contaminants by securing the cover to the skin of a person with the infusion device sealed inside.

DESCRIPTION OF THE PRIOR ART

Applicant is of course familiar with her earlier U.S. Pat. No. 5,336,204 which is also directed to a protective cover for infusion devices. While the cover of the '204 patent is certainly practical for protection due to its rigid body, it may have a slight disadvantage for proper adhesion on body contours due to its rigidity. In addition, the structure of the earlier cover was primarily for use to cover existing dressings that retain the catheter.

U.S. Pat. No. 3,900,026 employs a rigid body member. U.S. Pat. No. 3,782,378 requires a waist band to maintain an intravenous feeding tube where the tube passes under the shield which may allow moisture to penetrate beneath the shield. These are undesirable features.

SUMMARY OF THE INVENTION

One of the objects of the present invention is to provide a protective waterproof cover that is formed of soft pliable material that may easily follow the body contour and infusion devices where it is applied to seal the area and prevent moisture from entering the area to be protected.

Another object of the present invention is to provide a flexible protective cover that includes a transparent window that will allow visual inspection of the apparatus within the cover, such as a catheter, conventional Heparin lock, peripherally inserted central catheter (PICC line) or medical tubing and clamps as used in a subclavian catheter.

A further object of the present invention is to provide a flexible protective cover that includes an opening therein to receive apparatus wherein it is waterproof and moisture cannot enter the protected area wherein the appliance is located.

A still further object of the present invention is to provide a flexible protective cover that includes a mounting tab that contains a waterproof opening.

A yet further object of the present invention is to provide a flexible protective cover that includes a clear flexible transparent membrane to allow visual inspection of the protected area and which also can be stretched to receive and surround medical appliances such that a waterproof seal is provided and to conform to the apparatus inserted into the skin of a patient such as a Heparin lock or other types of intravenous (I.V.) technology.

Another object of the present invention is to provide a flexible protective cover that may include foam material such as cellular white foam of a cross-linked polyurethane material.

A further object of the present invention is to provide a flexible protective cover that includes hypoallergenic adhesive to effect a waterproof adherence to the skin without skin irritation.

A still further object of the present invention is to provide a flexible protective cover capable of being mass produced in quantities by die cutting the same.

These and other objects and advantages will become apparent from the following specification wherein details have been described for the competence of disclosure, without intending to limit the scope of the invention which is set forth in the appended claims.

BRIEF DESCRIPTION OF THE DRAWINGS

These advantages may be more clearly understood from the following detailed description and by reference to the drawing in which.

DETAILED DESCRIPTION OF THE PREFERRED EMBODIMENT

Figures 2, 3, 4:
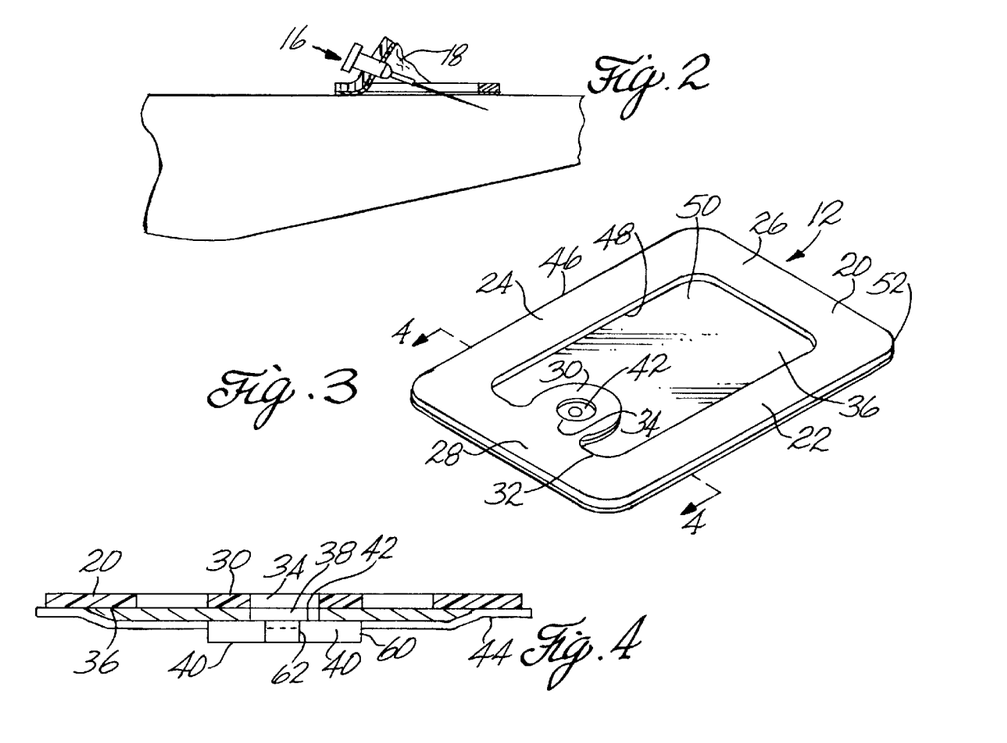
FIG. 2 is a side environmental view of the present invention in place upon the forearm of a patient.
FIG. 3 is a perspective view of a protective cover of the present invention.
FIG. 4 is a cross-sectional view of the present invention taken on lines 4—4 of FIG. 3.

A flexible protective cover generally designated 12 is seen as it is mounted on the forearm 14 of a person to protect infusion devices designated 16 a portion of which are contained inside the central section 18 as shown in FIG. 2.

The flexible protective cover 12 is preferably rectangular but can be made to any size or shape desired. The cover 12, as shown in FIGS. 1–6, is made of several layers of soft pliable material. When in use, the cover 12 preferably consists of two primary layers and an annular donut-shaped layer. In its pre-use stage, the cover consists of three primary layers and an annular donut-shaped layer, the third layer 44 being an adhesive cover that may be peeled off so that the adhesive on the bottom side of the first and second layers may be used to secure the cover 12 to the skin of the patient.

Figure 1:
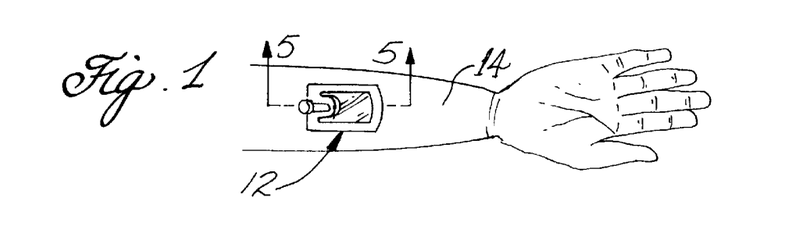
FIG. 1 is atop environmental view of the present invention in place upon the forearm of a patient.
Figure 5:
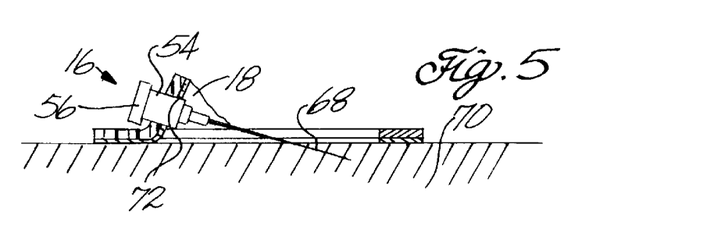
FIG. 5 is a cross-sectional view of the invention taken on lines 5—5 of FIG. 1.

The first layer 20 of the preferred embodiment has a first pair of spaced apart generally parallel elongated side walls 22 and 24 and a second pair of spaced apart generally parallel end walls 26 and 28 joining the side walls 22 and 24. The first layer 20 is a rectangular border flame with a circular mounting tab 30 protruding from an inner edge 32 of one of the rectangular ends (end wall 28 as shown in FIG. 3). The circular mounting tab 30 has a circular aperture 34 in its center where the edges of the circular aperture interact with a portion of the infusion device protruding out from the central section 18 to seal off the inner chamber from the outside air and its contaminants after the infusion device has been attached to the patient and the exterior portion of the infusion device has been pressed through the circular aperture 34 and the cover 12 has been attached to the patient as shown in FIGS. 1, 2 and 5. The second layer 36 is a thin transparent sheet of plastic-like material that allows the user to view and visually monitor the status of the interaction between the infusion device 16 and the patient into which it has been inserted. The transparent sheet 36 adheres to a portion of the bottom side of the first layer 20 and has a circular hole 38 in the identical position as the circular aperture 34 of the first layer. The annular donut-shaped layer 40 is a partial layer and is made from a sheet of elastomeric film and fits over the bottom side of the mounting tab 30. The radius of the annular donut-shaped layer 40 is less than the radius of the first layer aperture 34 and second layer circular hole 38. The resultant excess portion of annular donut-shaped layer 40 forms a ring 42 inside the aperture 34 of the first layer and the second layer circular hole 38. A third layer is a release liner 44 with a top side made from a non-stick material which is easily pealed away and discarded thereby exposing the adhesive materials on the bottom side of the transparent second layer 36 and on the bottom side of the first layer 20 not affixed to the second layer 36. These adhesive materials are then attached to the patient's skin. Because the annular donut-shaped layer 40 is thicker than the third layer release liner 44, the annular donut-shaped layer 40 has a circular cut-out large enough for the annular donut-shaped layer 40 to mate with, but not interact with the third layer release liner 44.

The first layer 20 is a thin border frame with essentially an outside edge 46 and an inside edge 48 defining the cut-out portion of the first layer 50. The outer edge 46 is generally a rectangular shape, preferably with rounded comers 52 which allows for a more secure seal to the patient's skin. The exterior shape of the cover 12, defined by the outside edge 46 of the first layer 20, is not critical as long as it is sufficiently wide and elongated to cover the infusion device and catheter being used. The inside edge 48 or cut-out portion 50 preferably conforms to the exterior shape, but it may be of any shape just as long as there is a sufficient opening to view the type of infusion device or catheter or tubing that is housed inside. Protruding from an inner cut-out edge 32 of the border frame is a generally circular-shaped mounting tab 30, preferably with a radial axis located an equidistance from the inner edges of the elongated border frames 22,24 with a radius being less than the distance between the inner edges of the elongated border frame. Along the same radial axis as the circular mounting tab 30 is a circular aperture 34 with a radius less than the radius of the generally shaped circular mounting tab 30. The circular aperture 34 allows access to the central section 18 formed after the cover 12 is attached to the patient's skin. The inner edge of the circular aperture interacts with an exterior portion of the infusion device to seal off the central section 18 from the outside air once the infusion device has been attached to the patient and the exterior portion fed through the circular mounting tab 30 and the cover 12 has been placed on top of the interior portion of the infusion device and attached to the patient. The bottom side of the first layer 20 is laminated with a layer of adhesive enabling the first layer 20 to be attached to the patient and the second layer 36 described below. The annular opening of the aperture 34 is preferably slightly less than the diameter of shank 54 of the Heparin lock hub 56 so that when the lock hub 56 is inserted further water proofing is achievable. The cover 12 is designed to sealably work with any type of lock. The presence of an actual hub is preferred, but is not necessary.

The first layer 20 border frame is preferably made from a cross linked polyethylene foam coated on the bottom side with an aggressive medical grade pressure-sensitive adhesive. The polyurethane foam material may be cut to the generally rectangular shape described above and illustrated or can be cut to any alternate shape as is deemed desirable.

The second layer 36 is a sheet of clear film with outer edges essentially defined by the outer edge 46 of the border frame of the first layer 20. However, the second layer 36 preferably does not extend to the outer edges of the first layer 20. Preferably, the outer edges of the second layer are located approximately half way between the outer edge 46 and the inner edge of the first layer 20 thereby exposing both adhesives on the bottom sides of the first layer 20 and the second layer 36 to the skin of the patient when the cover 12 is secured to the patient. The top side of the second layer 36 is free of adhesive material and adheres to the first layer 20 via the adhesive applied to the bottom side of the first layer 20. The radial axis, and preferably the radius, of the second layer circular hole 38 is identical to that of the first layer aperture 34. Alternatively the clear film of layer two 36 may have the corresponding second layer circular hole 38 left intact with a cross-cut as a replacement. Adhesive has been applied to the bottom side of the second layer 36 for adhesion to both the annular donut-shaped layer 40 and third layer 58. The adhesive is preferably hypoallergenic to avoid skin irritation and is waterproof so that the area of the skin sealed within the central section 18 will be free of moisture that might cause infection.

The second layer 36 is preferably made from a clear urethane film with medical pressure-sensitive acrylic adhesive coated on the bottom side. The urethane is a stretchably clear film which is highly breathable with a skin-like feel, is an excellent barrier to fluids, is soft and comfortable and has a high Moisture Vapor Transmission Rate (M.V.T.R). As such, the clear urethane film will be waterproof and will prevent water and contaminants from entering the inner chamber while simultaneously allowing trapped moisture, gases, etc. to escape. This prevents permanent condensation from building up on the bottom side of the clear film which would otherwise visually obscure and interfere with the ability of the user to monitor the interaction of the infusion or other medical devices with the patient's skin and which would promote infection.

Preferably, the annular donut-shaped layer 40 and the third layer 58 mateably interact to generally form the shape defined by the outer edge of the border frame first layer 20, yet maintain sufficient separation such that they do not interact with one another. Both the annular donut-shaped layer 40 and third layer 58 directly adhere to the bottom side of the second layer's 36 urethane film. The third layer 58 also directly adheres to the adhesive on the bottom side of the first layer 20 at the outer edges of the first layer where the second layer 36 stops short of the first layer's outer edges as shown in FIG. 4.

The annular donut-shaped layer 40 is defined by an outer radius 60 and an inner radius 62. Preferably, the outer radius is essentially the same as the outer radius of the generally circular aperture 34 of the first layer with an identical radial axis as the aperture 34 of the first layer. The inner radius 62 is preferably about half that of the radius of the inner radius of the aperture 34 thus forming a third layer ring 42 inside the inner radius of the aperture 34 of the first layer and the corresponding second layer circular hole 38. The third layer ring 42 is defined by the inner radius of the aperture 34 of the first layer and by the inner edge of the ring. The third layer donut-shape 44 is adhered directly to the bottom side of the second layer 36 such that the radial axis of the donut-shape 44 is essentially identical to the radial axis of the aperture 34 of the first layer and the corresponding second layer circular hole 38. Like the annular opening of the aperture 34 of the first layer, the inner radius of the donut-shape is less than the diameter of shank 54 of the Heparin lock hub 56 so that when the hub 56 is inserted further water proofing is achievable.

The annular donut-shaped layer 40 is preferably made from a thermoplastic elastomeric sheet. The medical grade elastomeric film possesses the ability to stretch while maintaining sufficient resilience to return to its normal or original size after being stretched. This resilience creates a watertight seal around the portion of the infusion device inserted through the annular donut-shaped layer 40 thereby maintaining the necessary water tight and air tight seal. No adhesive is applied to the annular donut-shaped layer 40. It is secured to the second layer 36 by the adhesive that is applied to the bottom side of the second layer.

Figure 6:
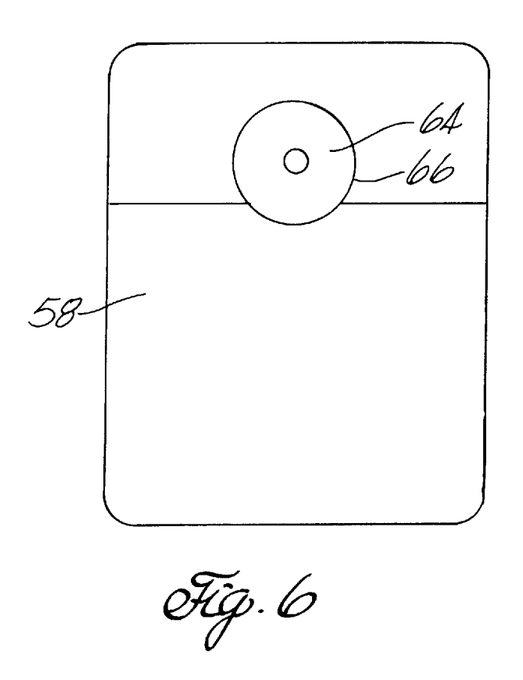
FIG. 6 is a bottom plan view of the present invention.
Figure 7:
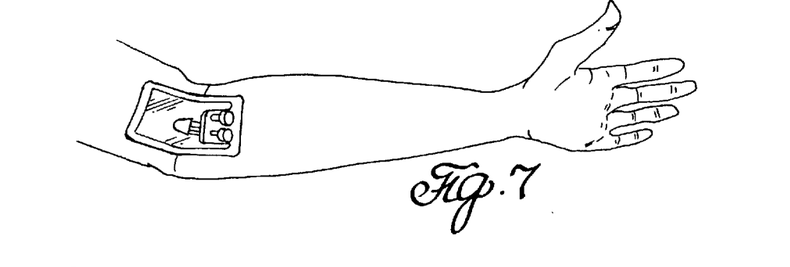
FIG. 7 is atop environmental view of an alternative embodiment of the present invention in use with a peripherally inserted central catheter (PICC line) and placed upon the arm of a patient.
Figures 8, 9:
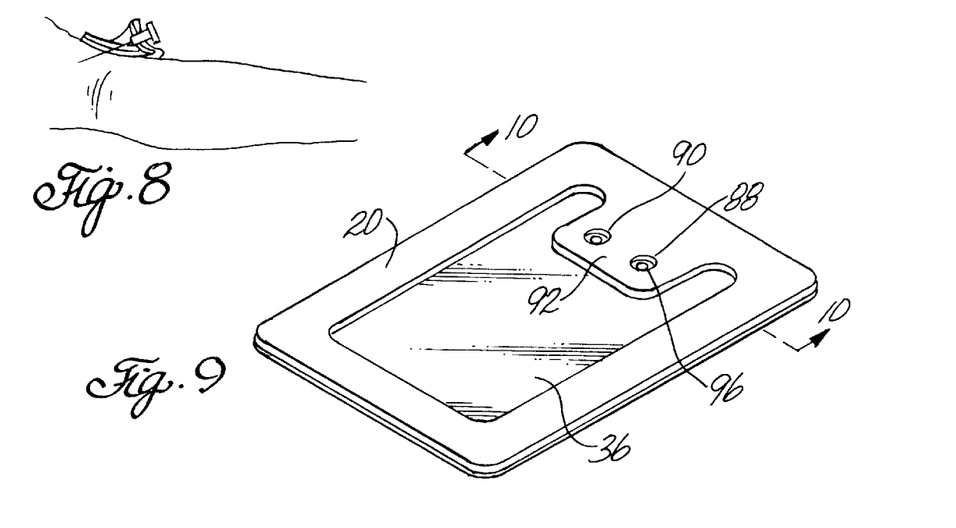
FIG. 8 is a view taken on lines 8—8 of FIG. 7.
FIG. 9 is a perspective view of another embodiment of the protective cover of the present invention in use with a subclavian catheter.
Figure 10:
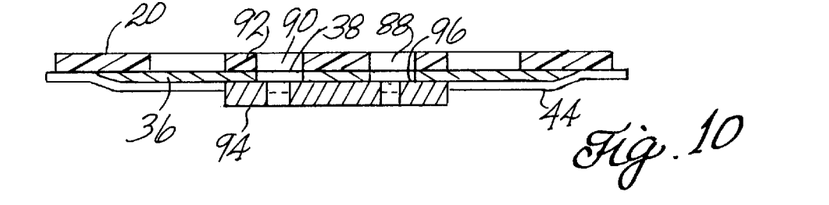
FIG. 10 is a cross-sectional view of the invention taken on lines 10—10 on FIG. 9.
Figure 11:
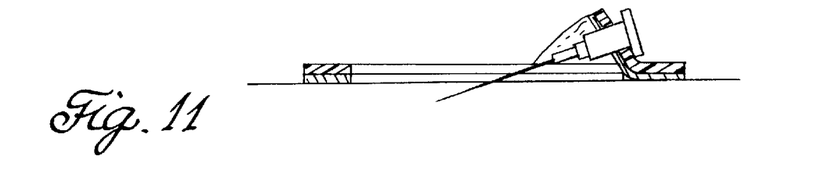
FIG. 11 is a side environmental view of the present invention is place upon the forearm of a patient.

Preferably, the third layer release liner 58 is made from standard siliconized kraft release paper 50#. The outer edge of the third layer is essentially defined by the outer edge of the first layer 20 with the outer edge of the third layer being slightly larger thereby allowing the user to easily peal away and discard the release liner 58. The third layer 58 preferably has a circular cut-out 64 slightly larger than the outer edge 66 of the annular donut-shaped layer 40 as shown in FIG. 6. The radial axis of the missing circular cut-out 64 is essentially identical to the radial axis of the annular donut-shaped layer 40, and the radius is slightly larger to allow the annular donut-shaped layer 40 to mateably fit inside the circular cut-out 64 of the third layer such that the third layer and the annular donut-shaped layer 40 do not interact. To facilitate the easy removability of the release liner 58, the release liner is preferably cut cross-wise from its elongated sides as shown in FIG. 6.

The infusion device 16 preferably includes a conventional catheter needle 68, see FIG. 5, which is inserted into the skin 70 of a patient into a vein. The needle 68 includes a conventional Heparin lock hub 56 so that a syringe (not shown) may be fitted into the lock hub 56 and an appropriate drug injected into the patient, or tubing fitted for fluid hydration or for blood withdrawal.

Due to the fact that Heparin users do not have to have a constant continuous infusion of Heparin, a lock has been developed so that the catheter may be left in the arm and the dosage may be applied when required without the need to make new punctures in the skin 70.

Thus in practice the catheter needle 68 may be inserted into the skin 70 and the removable third layer 58 of the cover 12 is then removed. The mounting tab 30 of the cover 12 is bent upwardly, see FIG. 5, and the Lock hub 56 is inserted through the aperture 34. The material of the cover 12 being resilient, the material around the aperture 34 may be contorted and stretched so that a portion of the lock 56 may pass through the aperture 34 and will seat in the lock annular recess 72. With the aperture 34 diameter being slightly smaller than the recess 72 a good waterproof seal may be achieved.

As can be seen in FIGS. 1, 2 and 5 the hub 56 projects outward of the mounting tab 30 so easy access is available for administering the required dosages at the times necessary yet leaving the infusion device free of moisture.

With the mounting tab 30 elevated it will be noted that the clear plastic film being relatively tight on the cover 12, it will adhere to the parts of the lock 56 thereunder, see FIG. 5. This will not only assure a greater water proofing, but will also act to stabilize the infusion device 16 while it is on a patient's body.

As the flexible cover 12 is secured to the skin 70 by means of the adhesive on the bottom sides of the first layer 20 and second layer 36, the seal around the Heparin lock tab shank 54 seals off the central section 18, creating a completely water proof central section. In that way infusion devices as well as other medical devices may be maintained on a patient's body for a longer period than usual as the chances of infection are reduced and the chances of the device being dislodged are reduced.

Figure 12:
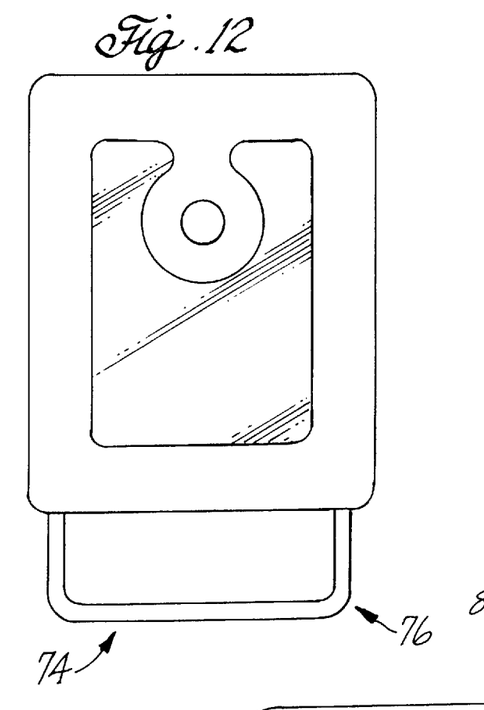
FIG. 12 is a top environmental view of a modified version of the protective cover with a double tape system for patients with ultra-sensitive skin before being placed in use.
Figure 13:
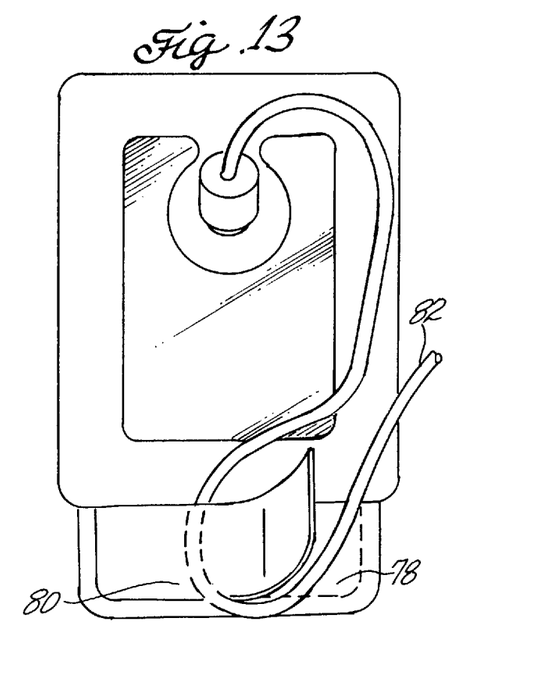
FIG. 13 is a top environmental view of a modified version of the protective cover with a double tape system for patients with ultra-sensitive skin after being placed in use.

A modification of the above described invention includes an extension of one of the frame border sides, preferably the side opposite the attached to the aperture 34. The extension can be accomplished by increasing the width of the frame border side being extended (not shown) or by placing a double layered tape system 76 immediately adjacent to the border frame side where the extension is desired, as shown in FIGS. 12 and 13.

The double layered tape system consists of two layers. The bottom layer 78 is directly attached to the skin of the patient by an adhesive that has been pre-applied to the bottom side of the bottom layer. Preferably the adhesive is hypoallergenic to avoid skin irritation. Preferably, the top side of the bottom layer is also covered with adhesive.

The top layer 80 is preferably adhesive free and is capable of adhering to the adhesive applied to the top side of the bottom layer 78. However, the top layer 80 is preferably only partially acceptable to the adhesive so that it can be releasably affixed and used as many times as needed to secure the exterior extensions 82 of the infusion devices, catheters and other medical devices away from the patient's skin. This is especially important for older patients who can typically have extremely thin and brittle skin which is easily damaged. By securing the exterior extensions 82 in a manner such that they do not interact with the skin of the patients, irritation, skin breakage and infection to the areas of skin immediately surrounding the cover 12 can be avoided.

Alternatively, the double tape system 76 can be applied directly to the frame border that has been extended (not shown) or a single reusable piece of tape that adheres to the top of the frame border while retaining the ability to be releasably affixed, repeatedly as needed.

Figure 14:
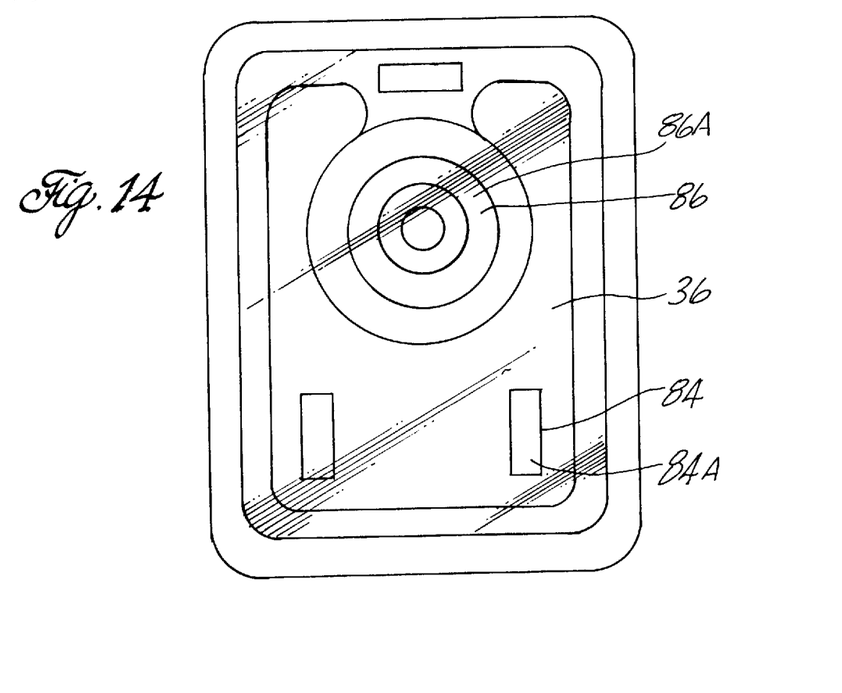
FIG. 14 is a bottom environmental view of a modified version of the protective cover with a wicking pad and/or antimicrobial pad.

An alternative embodiment of the invention is shown in FIG. 14. Wicking pad 84 has been attached to the adhesive laced bottom side of the urethane layer two 36. Preferably, the bottom side of the wicking pad 84 does not contain an adhesive and either rests directly on the skin or is attached to the urethane layer two 36 in such a manner as to be elevated off the skin when the cover is in use. The wicking pad can also be shaped as a ring 86 and applied to the bottom side of the annular donut-shaped layer 40 such that the radial axis of the wicking pad ring 86 is essentially identical to the radial axis of the aperture 34 of the first layer. The wicking pad in the shape of a ring 84 is defined by an outer radius and an inner radius such that the outer radius is less than the radius of the mounting tab 30 of the first layer and the inner radius is greater than the inner radius of the annular donut-shaped layer 40.

The wicking pad preferably is made of an absorbent hydrophilic polyurethane foam pad and is designed to draw moisture away from the injection site. The wicking pad is therefore ideal for absorbing excess moisture that may become trapped in the inner chamber during the use-life of the cover. Because the wicking pad is preferably free of adhesive on the bottom side where it would normally contact the skin of a patient, upon removal, it preserves regenerating tissue.

The wicking pads can be placed in the preferred positions as indicated or they can be placed anywhere in the central section of the cover when in use. Alternatively, the wicking pads can be applied directly to the skin with adhesive if so desired.

In an additional embodiment of the invention, the wicking pad 84 and ring 86 can be replaced with an antimicrobial pad 84A and ring 86A. Preferably the antimicrobial pad contains chlorhexidine gluconate (CHG). The use of an antimicrobial pad in the central section of the cover helps eliminate the potential growth of bacteria or other infection promoting entities. Alternatively, the wicking pad and the antimicrobial pad can be simultaneously applied to the bottom side of the urethane film layer two or to the bottom side of the donut-shaped third layer.

In yet another alternative, the properties of the wicking pad and the antimicrobial pad can be combined into one patch with both properties and affixed to the bottom side of the urethane film layer two 36 or to the bottom side of the annular donut-shaped layer 40 as shown in FIG. 14. Whether applied separately or in a combined form, the wicking pad and antimicrobial pad can be placed anywhere inside the central section and can also be applied directly to the skin with an adhesive if so desired. The CHG of the antimicrobial pad can also be combined with the adhesive on the bottom side of the clear urethane film of layer two thereby eliminating the use of a pad to hold the CHG. This alternative embodiment can be adapted to be used simultaneously with the alternative embodiment for fragile skin described above and shown in FIGS. 12 and 13.

In another embodiment of the invention, the mounting tab 30 of the first layer is replaced with an essentially rectangular protrusion 92 emanating from the same frame border side as shown in FIGS. 7–11. In this embodiment of the invention, the single aperture 34 is replaced with at least two separate holes 88 and 90. Additional holes can be incorporated as the need arises. Likewise the one hole cut into the second urethane clear film of layer two is replace with holes with identical radial axis' and radius' as the holes incorporated into the first layer. Likewise the annular donut-shaped layer 40 is replaced with an essentially rectangular layer 94 essentially identical to the rectangular protrusion 92 emanating from the side of the frame border of layer one 20. The rectangular layer 94 would also have two holes (88 and 90) with essentially identical radial axis and with radius' approximately half of the radius' of the holes in the first layer. Similar to the one hole version of the invention, these two holes would each leave a ring 96 of the rectangular layer exposed. These two rings would be defined by an inner and an outer edge. The radius of the inner edge being less than the radius of the holes of the first layer and the outer radius being essentially identical to the radius of the hole of the first layer.

Figure 15:
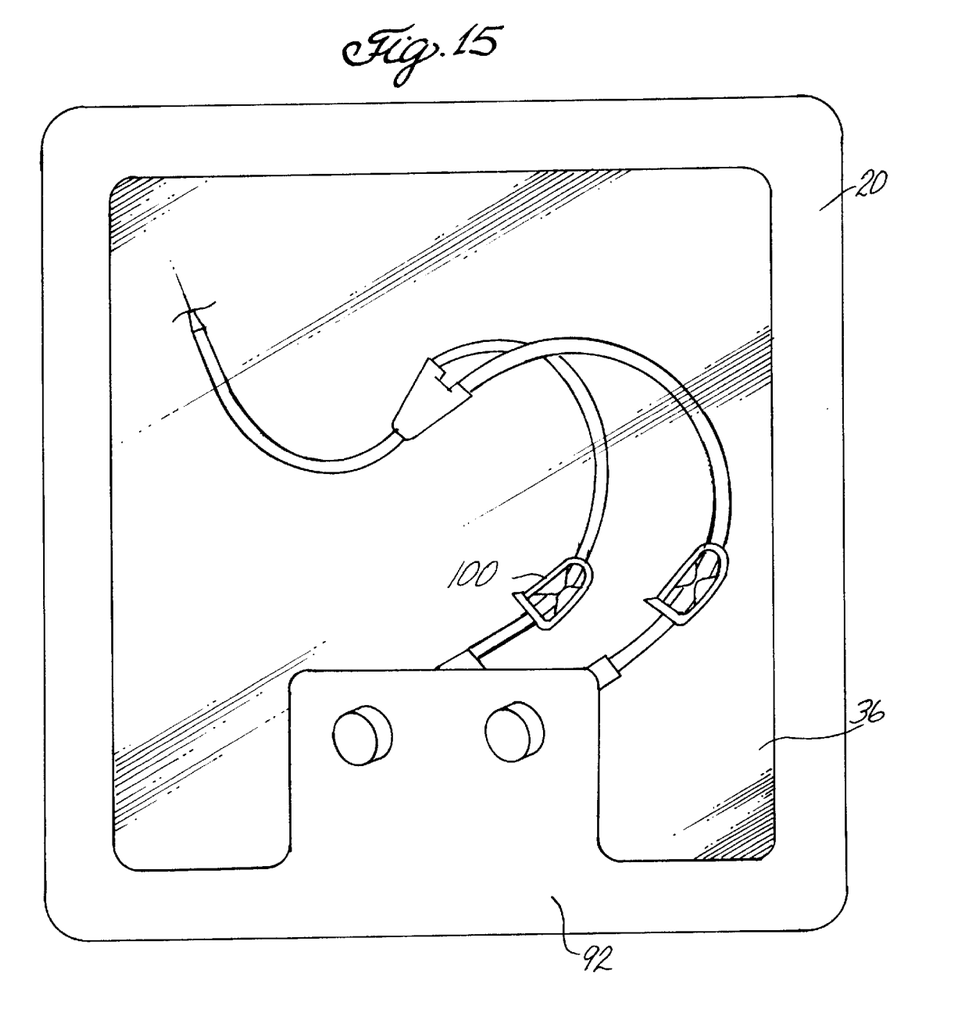
FIG. 15 is atop environmental view of a modified version of the protective cover for use with a subclavian catheter.

The double holed version of the invention as described above and shown in FIGS. 7–11 is easily adapted to use with a peripherally inserted central catheter (PICC line), or with a subclavian catheter as shown in FIG. 15. The excess tubing 98 with clamps 100 can be housed inside the central section 18 of the cover whereby the clamps 100 can be accessed through the clear urethane film layer two 36 simply by grasping them and clamping them shut if the need should arise.

What is claimed is:

1. A replaceable flexible protective cover for an infusion device wherein said infusion device may include a Heparin lock with an annular shank portion presenting an exterior portion and an interior portion and catheter means inserted within the skin of a person and joined to said interior portion, said cover comprising:

a resilient transparent waterproof membrane covering adapted to be stretched and distorted by said Heparin lock to engage portions thereof, to cover and to waterproof and stabilize the device;

an opening within said membrane covering adapted to be contorted to allow said annular shank portion of said lock to receive and passe therethrough and to interact in a manner wherein a waterproof seal is created; and an adhesive on said membrane covering for releasably affixing said protective cover to the skin of a person and to conform to and seal to said lock.

2. A replaceable flexible protective cover as defined in claim 1 wherein said cover:

includes a flexible frame member of a size adequate to surround said interior portion of said Heparin lock and having a top side and a bottom side.

3. A replaceable flexible protective cover as defined in claim 2 wherein:

said flexible frame member is formed from a plastic material.

4. A replaceable flexible protective cover as defined in claim 2 wherein:

said flexible frame member is formed of cellular white foam of a cross-linked polyurethane.

5. A replaceable flexible protection cover as defined in claim 2 wherein:

the frame includes a first pair of parallel spaced apart side walls and a second pair of parallel spaced apart end walls extending between said side walls.

6. A replaceable flexible protection cover as defined in claim 2 wherein:

a mounting tab having a top and bottom surface appends inwardly from said end wall into the space within said frame and at least one opening therethrough, said mounting tab being adapted to be bent upwardly to present a face generally normal to the angle of said Heparin lock wherein said lock passes through said opening with said opening interacting with said lock to seal the interior of said frame against the entry of outside moisture with said exterior portion capable of receiving an injection device insertable into said infusion device.

7. A replaceable flexible protection cover as defined in claim 6 wherein:

the transparent waterproof membrane is attached to the bottom side of said frame.

8. A replaceable flexible protection cover as defined in claim 7 wherein:

an annular seal member is mounted beneath the bottom surface of said mounting tab surrounding said opening to increase thickness and impart a further waterproofing capability to said cover when said Heparin lock is inserted therein.

9. The arrangement defined in claim 7 wherein:
a double tape system extends off one of the peripheral walls to secure extraneous medical tubing, or equivalent, away from the skin of the patient, said double tape system comprising:
  a bottom strip with a top side and a bottom side, said bottom side attached directly to the skin of the patient by adhesive;
  a top strip with a top side and a bottom side; and
said bottom side of said top strip and said top side of said bottom strip interacting in a releasably affixing manner.

10. The arrangement defined in claim 7 wherein:
the adhesive on said bottom side of said bottom strip is hypoallergenic and is covered with a removable protection sheet until ready to use.

11. The arrangement defined in claim 7 wherein:
a flexible and absorbent wicking pad is attached to said flexible protective cover in such a manner to ensure that the wicking pad is inside the central section and exposed to the patient's skin when the replaceable flexible protective cover is attached to the skin of the patient, said wicking pad consisting of:
  side edges defining a geometrical shape;
  a top and bottom surface, said top surface attached to said flexible protective cover.

12. The arrangement defined in claim 7 wherein:
an annular seal member is mounted beneath the bottom surface of said mounting tab surrounding said opening to increase thickness and impart a further waterproofing capability to said cover when said Heparin lock is inserted therein; and
said flexible and absorbent wicking pad is attached to the bottom side of either said annular seal member or to the bottom surface of said transparent waterproof member.

13. The arrangement defined in claim 7 wherein:
said flexible and absorbent wicking pad is attached to the bottom side of said transparent waterproof member.

14. The arrangement defined in claim 7 wherein:
a flexible antimicrobial pad is attached to said transparent waterproof member in such a manner to ensure said antimicrobial pad is inside the central section and exposed to the patient's skin when the replaceable flexible protective cover is attached to the skin of the patient, said antimicrobial pad consisting of:
  side edges defining a geometrical shape;
  a top and bottom surface, said top surface attached to said flexible protective cover.

15. The arrangement defined in claim 7 wherein:
said flexible antimicrobial pad is attached to the bottom side of said flexible, transparent waterproof member.

16. The arrangement defined in claim 7 wherein:
an annular seal member is mounted around said opening in said mounting tab to increase thickness and impart a further waterproofing capability to said cover when said Heparin lock is inserted therein; and
said flexible antimicrobial pad is attached to the bottom side of said annular seal member.

17. The arrangement defined in claim 7 wherein:
said flexible antimicrobial pad contains chlorhexidine gluconate.

18. The arrangement defined in claim 7 wherein:
said flexible antimicrobial pad possesses absorbent capabilities essentially equivalent to those of the wicking pad.

19. The arrangement defined in claim 7 wherein:
an antimicrobial material is applied to the bottom side of said transparent waterproof member.

20. A replaceable flexible protection cover as defined in claim 6 wherein:
said adhesive on said transparent waterproof membrane is hypoallergenic and is covered with a removable protection sheet until ready for use.

21. A replaceable flexible protection cover as defined in claim 1 wherein:
said opening is an annular opening in said membrane.

22. A replaceable flexible protection cover as defined in claim 1 wherein:
said opening is a cross cut opening.

23. A replaceable flexible protection cover as defined in claim 1 wherein:
the adhesive on said transparent waterproof membrane is hypoallergenic and is covered with a removable protection sheet until ready for use.

24. A replaceable flexible protective cover for medical equipment which may include medical equipment such as infusion devices, clamps, tubing or other devices having a shank portion defining an exterior portion and an interior portion, the replaceable flexible protective cover comprising, in combination:
  a flexible, resilient top layer having a top surface and a bottom surface and a peripheral wall having a predetermined geometrical configuration with peripheral walls defining a central section therebetween;
  a first flexible, resilient, waterproof adhesive layer substantially coextensive with said top layer and having an inner surface on said bottom surface of said top layer and a outer surface, and said outer surface adapted to be adhered to the middle layer;
  a flexible, resilient, waterproof middle layer having a top surface and a bottom surface, said top surface adhering to said bottom surface of said top layer;
  a second flexible, resilient, waterproof adhesive layer substantially coextensive with said middle layer and having an inner surface on said bottom surface of said middle layer and a outer surface, and said outer surface adapted to be adhered to the skin of the person; and
  a flexible mounting tab having a top and bottom surface appending inwardly from said peripheral wall into the space within said frame, and at least one opening therethrough and said mounting tab adapted to be bent upwardly to present a face generally normal to the angle of said shank portion wherein said shank portion passes through said opening with said opening interacting with said shank portion to seal the interior of said frame against the entry of moisture with said exterior portion capable of receiving an injection device to connect to said medical equipment connected to said person.

25. The arrangement defined in claim 24 wherein:
said peripheral wall of said top layer having a front wall portion, a pair of spaced apart side wall portions and a back wall portion spaced from said front wall portion defining a central section therebetween.

26. The arrangement defined in claim 24 wherein:
said middle layer is transparent, said second adhesive layer is hypoallergenic and further comprising a removable cover layer on said outer surface of said second adhesive layer for protecting said second adhesive layer for the condition of said second adhesive layer not affixed to the skin of the person.

27. The arrangement defined in claim 24 wherein:
an annular seal member is mounted around said opening in said mounting tab to increase thickness and impart further waterproof quality to said cover where said shank portion is inserted therein.

28. The arrangement defined in claim 27 wherein:
said removable cover layer having a cut-out portion corresponding to the shape of said annular seal member.

29. The arrangement defined in claim 24 wherein:
said top layer is a cellular white foam layer of a cross linked polyurethane.

30. The arrangement defined in claim 24 wherein:
a double tape system extends off said peripheral walls to secure tubing or other extraneous medical equipment away from the skin of the patient, said double tape system comprising:
a bottom strip with a top side and a bottom side, said bottom side attached directly to the skin of the patient by adhesive;
a top strip with a top side and a bottom side; and
said bottom side of said top strip and said top side of said bottom strip interacting in a releasably affixing manner.

31. The arrangement defined in claim 30 wherein:
the adhesive on said bottom side of said bottom strip is hypoallergenic and is covered with a removable protection sheet until ready to use.

32. The arrangement defined in claim 24 wherein:
a flexible and absorbent wicking pad is attached to said flexible protective cover in such a manner to ensure that the wicking pad is inside the central section and exposed to the patient's skin when the replaceable flexible protective cover is attached to the skin of the patient, said wicking pad consisting of:
side edges defining a geometrical shape;
a top and bottom surface, said top surface attached to said flexible protective cover.

33. The arrangement defined in claim 32 wherein:
an annular seal member is mounted beneath the bottom surface of said mounting tab surrounding said opening to increase thickness and impart further waterproof quality to said cover where said Heparin lock is inserted therein; and
said flexible and absorbent wicking pad is attached to the bottom side of said annular seal member.

34. The arrangement defined in claim 32 wherein:
said flexible and absorbent wicking pad is attached to the bottom side of said flexible, resilient waterproof middle layer.

35. The arrangement defined in claim 24 wherein:
a flexible antimicrobial pad is attached to said flexible protective cover in such a manner to ensure said antimicrobial pad is inside the central section and exposed to the patient's skin when the replaceable flexible protective cover is attached to the skin of the patient, said antimicrobial pad consisting of:
side edges defining a geometrical shape;
a top and bottom surface, said top surface attached to said flexible protective cover.

36. The arrangement defined in claim 35 wherein:
said flexible antimicrobial pad is attached to the bottom side of said flexible, resilient waterproof middle layer.

37. The arrangement defined in claim 35 wherein:
an annular seal member is mounted around said opening in said mounting tab to increase thickness and impart further waterproof quality to said cover where said Heparin lock is inserted therein; and
said flexible antimicrobial pad is attached to the bottom side of said annular seal member.

38. The arrangement defined in claim 35 wherein:
said flexible antimicrobial pad contains chlorhexidine gluconate.

39. The arrangement defined in claim 35 wherein:
said flexible antimicrobial pad provides absorbent capabilities essentially equivalent to those of the wicking pad.

40. The arrangement defined in claim 24 wherein:
said mounting tab has two openings therethrough.

41. The arrangement defined in claim 40 wherein:
one or more seal members are mounted around said openings in an annular fashion in relation to said openings to increase thickness and impart further waterproof quality to said cover where said shank portion is inserted therein.

42. The arrangement defined in claim 40 wherein:
said antimicrobial material is applied to the bottom side of the middle layer.

43. A replaceable flexible protective cover for medical equipment which may include an infusion device, clamps and/or tubing having a shank portion defining at least an exterior portion, the replaceable flexible protective cover comprising, in combination:
a flexible, resilient top layer having a top surface and a bottom surface and a peripheral wall having a predetermined geometrical configuration with peripheral walls defining a central section therebetween;
a first flexible, resilient, waterproof adhesive layer substantially coextensive with said top layer and having an inner surface on said bottom surface of said top layer and a outer surface, and said outer surface adapted to be adhered to the middle layer;
a flexible, resilient, waterproof middle layer having a top surface and a bottom surface, said top surface adhering to said bottom surface of said top layer;
a second flexible, resilient, waterproof adhesive layer substantially coextensive with said middle layer and having an inner surface on said bottom surface of said middle layer and a outer surface, and said outer surface adapted to be adhered to the skin of the person;
a flexible mounting tab having a top and bottom surface appending inwardly from said peripheral wall into the space within said frame, and at least two openings therethrough and said mounting tab adapted to be bent upwardly to present a face generally normal to the angle of said shank portion wherein said shank portion passes through said opening with said opening interacting with said shank portion to seal the interior of said frame against the entry of outside moisture with said exterior portion capable of receiving an injection device to connect to said medical equipment connected to said person; and
a seal member mounted to the bottom of the middle layer directly below said mounting tab to increase thickness and impart further waterproof quality to said cover where said Heparin locks are inserted therein.

44. The arrangement defined in claim 43 wherein:
said second flexible, resilient, waterproof adhesive layer is hypoallergenic and is covered with a removable protection sheet until ready to use.

* * * * *

UNITED STATES PATENT AND TRADEMARK OFFICE
CERTIFICATE OF CORRECTION

PATENT NO. : 5,885,254
DATED : March 23, 1999
INVENTOR(S) : Melanie E. Matyas

It is certified that error appears in the above-identified patent and that said Letters Patent is hereby corrected as shown below:

Column 1, line 27, replace "a waist" with -- an elastic --.
Column 2, lines 14,27,49, replace "atop" with -- a top -- (all occurrences).
Column 2, line 38, after "invention" replace "is" with -- in --.
Column 3, line 5, replace "flame" with -- frame --.
Column 3, line 32, replace "pealed" with -- peeled --.
Column 3, line 45, replace "comers" with -- corners --.
Column 5, line 36, replace "peal" with -- peel --.
Column 7, line 52, change "replace" to -- replaced --.
Column 8, line 23, replace "passe" with -- pass --.
Column 10, lines 33,41, replace "a outer" with -- an outer --
 (both occurrences).
Column 10, line 46, replace "frame" with -- central section --.
Column 10, line 52, after "interior" delete -- of said frame --.
Column 11, line 44, replace "Heparin lock" with -- shank portion --.
Column 12, line , replace "Heparin lock" with -- shank portion --.
Column 12, lines 36,44, replace "a outer" with -- an outer --
 (both occurrences).
Column 12, line 48, replace "frame" with -- central section --.

UNITED STATES PATENT AND TRADEMARK OFFICE
CERTIFICATE OF CORRECTION

PATENT NO. : 5,885,254
DATED : March 23, 1999
INVENTOR(S) : Melanie E. Matyas

It is certified that error appears in the above-identified patent and that said Letters Patent is hereby corrected as shown below:

Column 12, lines 53,54, after "interior" delete -- of said frame --.
Column 12, line 61, replace "Heparin locks" with -- shank portions --.

Signed and Sealed this

Twentieth Day of February, 2001

Attest:

NICHOLAS P. GODICI

Attesting Officer

Acting Director of the United States Patent and Trademark Office